United States Patent [19]
Gilman et al.

[11] Patent Number: 4,712,580
[45] Date of Patent: Dec. 15, 1987

[54] EXHALATION VALVE ASSEMBLY

[75] Inventors: Keith Gilman, W. Cajon Valley; Bruce W. Lutz, Hesperia, both of Calif.

[73] Assignee: Intertech Resources Inc., Bannockburn, Ill.

[21] Appl. No.: 842,670

[22] Filed: Mar. 21, 1986

[51] Int. Cl.$^4$ .......................................... F16K 15/14
[52] U.S. Cl. ............................. 137/512.15; 137/859; 137/906; 137/908
[58] Field of Search ............... 137/496, 908, 859, 906, 137/528, 512.15, 516, 269, 510; 251/61.1; 128/205.24

[56] References Cited

U.S. PATENT DOCUMENTS

| | | | |
|---|---|---|---|
| 1,592,191 | 7/1926 | Etzelt . | |
| 2,877,791 | 3/1959 | Rich | 251/61.1 X |
| 3,078,066 | 2/1963 | Moore | 137/510 X |
| 3,262,447 | 7/1966 | Burke . | |
| 3,490,479 | 1/1970 | Mott et al. | 251/61.1 X |
| 3,942,547 | 3/1976 | Pfitzner . | |
| 4,190,045 | 2/1980 | Bartels . | |
| 4,214,601 | 7/1980 | Sama . | |
| 4,241,756 | 12/1980 | Bennett et al. | 137/496 |
| 4,267,832 | 5/1981 | Hakkinen . | |
| 4,284,104 | 8/1981 | Beghini . | |
| 4,454,893 | 6/1984 | Orchard | 251/61.1 |
| 4,543,935 | 10/1985 | Tuckey | 137/510 X |

Primary Examiner—Martin P. Schwadron
Assistant Examiner—Stephen M. Hepperle
Attorney, Agent, or Firm—Marshall, O'Toole, Gerstein, Murray & Bicknell

[57] ABSTRACT

An exhalation valve assembly for use in a volume ventilator circuit is disclosed that comprises a valve body defining a chamber with a gas inlet conduit and a gas outlet conduit, both in flow communication with the chamber. A diaphragm extends across the chamber and selectively closes off the gas inlet conduit. A concentric ring support structure is disposed concentrically about the gas inlet conduit and is configured so as to support a portion of the diaphragm over the chamber.

6 Claims, 6 Drawing Figures

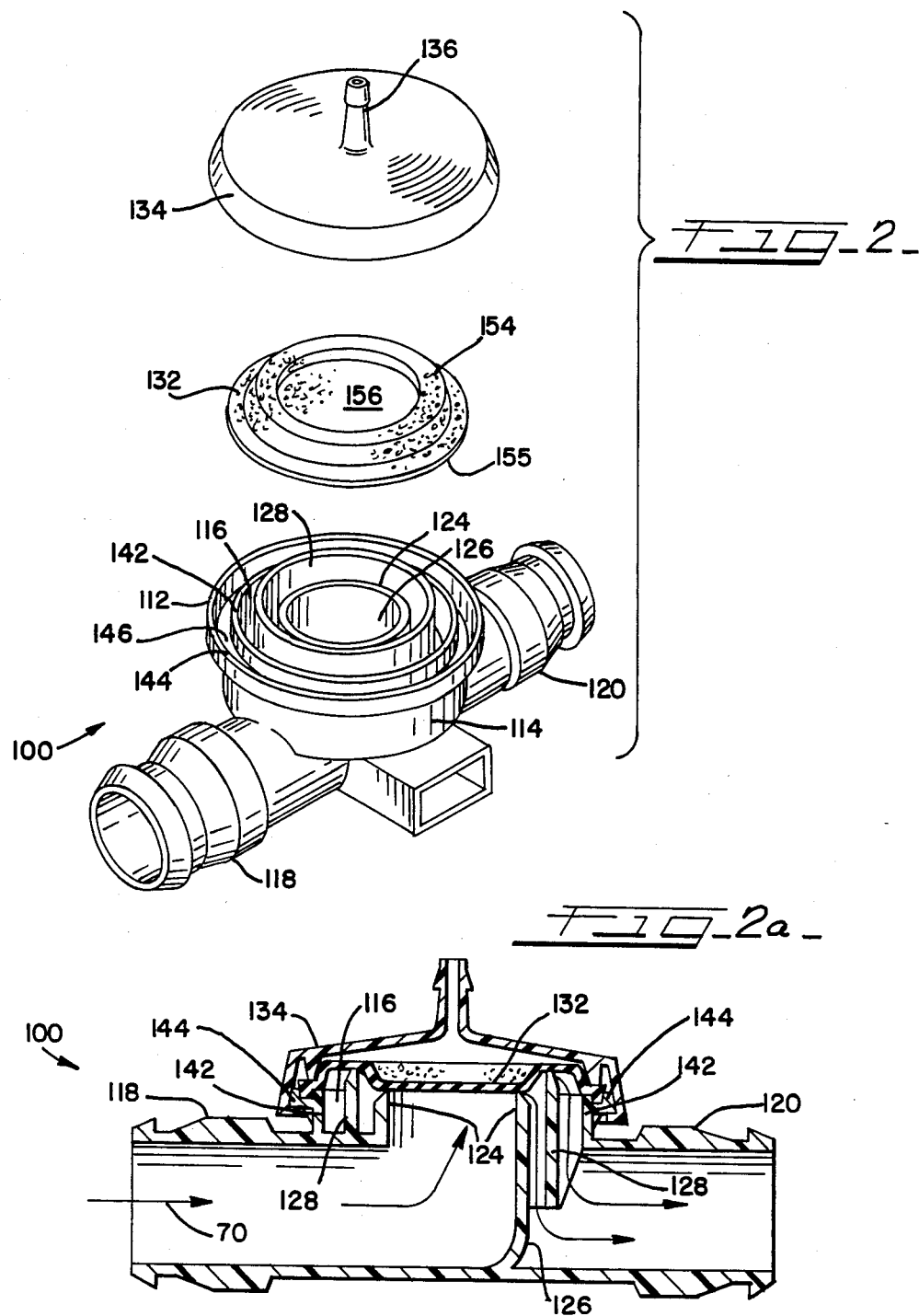

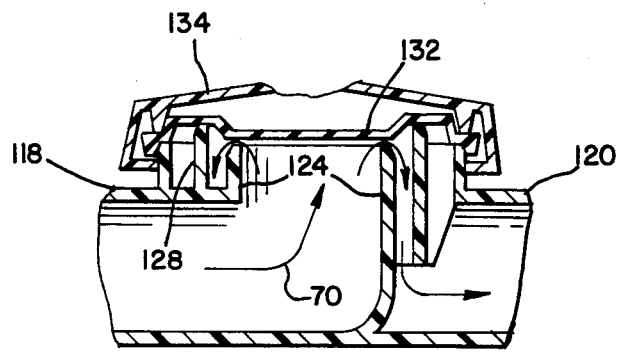
FIG_2b_
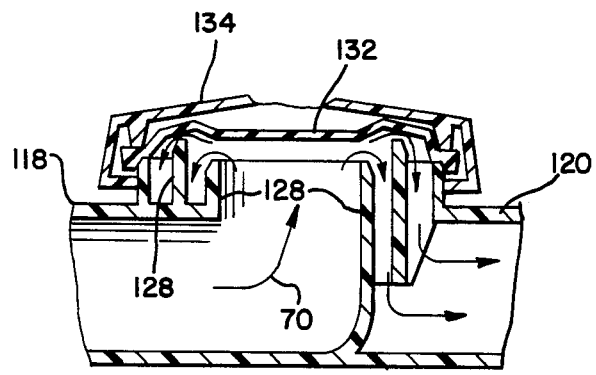
FIG_2c_

EXHALATION VALVE ASSEMBLY

BACKGROUND OF THE INVENTION

1. Field of the Invention

This invention relates to respiratory therapy devices and, more particularly, to the design and construction of an improved exhalation valve assembly that can be used in various volume ventilator circuits.

2. Description of the Prior Art

An example of a prior art exhalation valve assembly is disclosed in U.S. Pat. No. 4,241,756. As noted in that patent, volume ventilator circuits utilize an exhalation valve assembly to hold and maintain pressure within the circuit and selectively allow gases to be exhaled by the patient and to escape therefrom. Exhalation valve assemblies are comprised of a valve body having a gas inlet conduit, which forms a gas discharge port within the valve body, and a gas outlet conduit. A flexible diaphragm selectively closes off the discharge port during inhalation. When the patient exhales, the diaphragm is pushed away from the port so as to allow the exhaled gases to escape from the valve body through the gas outlet conduit.

Volume ventilators, in general, have different pressure holding capabilities depending on their particular application. One determinant of pressure holding capability is the ratio of the area of the diaphragm that extends across the chamber of the valve body (hereinafter referred to as "effective area") to the area of the gas discharge port. This ratio will hereinafter be referred to as the "valve area ratio."

One of the most widely used volume ventilators in the respiratory therapy field has a limited capability for holding elevated Positive End Expiration Pressure ("P.E.E.P.") when using a circuit with a valve assembly having a valve area ratio usually below 1.5. The valve assembly used in such a circuit is specifically designed to achieve a particular ratio and cannot be modified so as to be used in another circuit requiring a different ratio. Another popular volume ventilator is not dependent upon the valve area ratio for high P.E.E.P. pressures, but rather is dependent on the valve area ratio for low patient exhalation effort beyond P.E.E.P. pressures. The valve assembly is specifically designed to achieve the required valve area ratio and cannot be modified to provide a different ratio for use in a different machine. Thus, prior art volume ventilators have required the use of specifically designed valve assemblies in order to achieve the desired valve area ratio. Notwithstanding the increased costs of manufacturing one specific valve for one type of machine, the prior art has been unable to provide any interchangeability of such valve assemblies.

The prior art valve assembly disclosed in the previously mentioned patent provided a means of using the same exhalation valve assembly in volume ventilator circuits requiring different valve area ratios. This was accomplished by a removable ring member, which supported a portion of the diaphragm being used.

While this construction allowed great flexibility, it was often not fully utilized. That is, this prior art valve assembly was often not used without the ring member even though it could have been so used. In practice, the configuration most often used was to leave the ring member in place and use diaphragms of varying construction and material, thereby changing the pressure holding capability of the volume ventilator and the effective area of the diaphragm. This meant unnecessary complexity and unnecessarily greater manufacturing and parts costs. The present invention overcomes these problems by providing a valve assembly that provides for different pressure holding capabilities while eliminating the need for support members and for the removable ring member.

SUMMARY OF THE INVENTION

One object of the present invention is to provide an exhalation valve assembly that can be used in different volume ventilator circuits while incorporating a more simple construction than previous valve assemblies.

The exhalation valve assembly of the present invention is designed for use in gas flow circuitry such as a volume ventilator circuit. The valve assembly includes a valve body having a chamber in flow communication with the gas inlet conduit and the gas outlet conduit. The gas inlet conduit is configured to be coupled to a patient such that exhaled gases from the patient are directed through a gas discharge port into the chamber formed in the valve body. The gas outlet conduit directs the exhaled gas out of the chamber.

A diaphragm extends across the chamber formed in the valve body and is configured to selectively close off the discharge port. The diaphragm is held in position by a removable cap that permits easy replacement of the diaphragm with diaphragms of different configuration and construction. The cap includes a gas inlet port for introducing a gas into the area between the diaphragm and the cap.

In order to support the diaphragm, the prior art valve assembly used a plurality of upwardly extending strut members disposed around the chamber on the internal wall of the valve body, as well as using a portion of the valve body itself to support the diaphragm along its periphery. The strut members were used to support a removable ring member which supported a portion of the diaphragm from extending across the chamber, thereby reducing the effective area of the diaphragm. The present invention eliminates the strut members and removable ring member. Instead, the present invention incorporates a concentric wall disposed around the chamber a predetermined distance from the internal wall of the valve body. Depending on the particular diaphragm being used, the concentric wall or ring structure will come in contact with a portion of the diaphragm and thereby reduce the effective area of the diaphragm.

Use of the ring structure allows for the elimination of the upwardly extending support members and the associated removable ring member, resulting in reduced manufacturing costs and fewer parts. Further, there is no removable ring member that may be misplaced and the valve assembly is easier to use, since it is no longer necessary to train someone in utilizing the various combinations of ring member and diaphragm construction.

The concentric ring structure serves the same purpose as the upwardly extending support structure members and removable ring member, but improves upon the prior design. More specifically, during inhalation, the diaphragm closes off the discharge port, as before. Upon exhalation, the diaphragm is likewise disengaged from the discharge port. However, depending on the diaphragm used and the pressure created by introducing a gas through the inlet port of the cap, exhaled air may pass out of the chamber and into the outlet conduit on only one side of the ring structure or on both sides. Thus, in order to change the pressure holding capability of a volume ventilator circuit utilizing the present invention, one need merely remove the cap from the valve assembly, remove and replace the diaphragm, and replace the cap.

The novel features that are believed to be characteristic of the present invention, both as to its organization and method of operation, together with further objectives and advantages thereof, will be better understood from the following description considered in connection with the accompanying drawings in which a presently preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 2 is an exploded perspective view of the exhalation valve assembly of the present invention;

FIG. 2a is a cross section of the exhalation valve assembly of the present invention.

FIG. 2b is a fragmentary view illustrating the operation of the valve assembly; and FIG. 2c is another fragmentary view further illustrating the operation of the valve assembly.

DETAILED DESCRIPTION OF THE INVENTION

Figure 1:
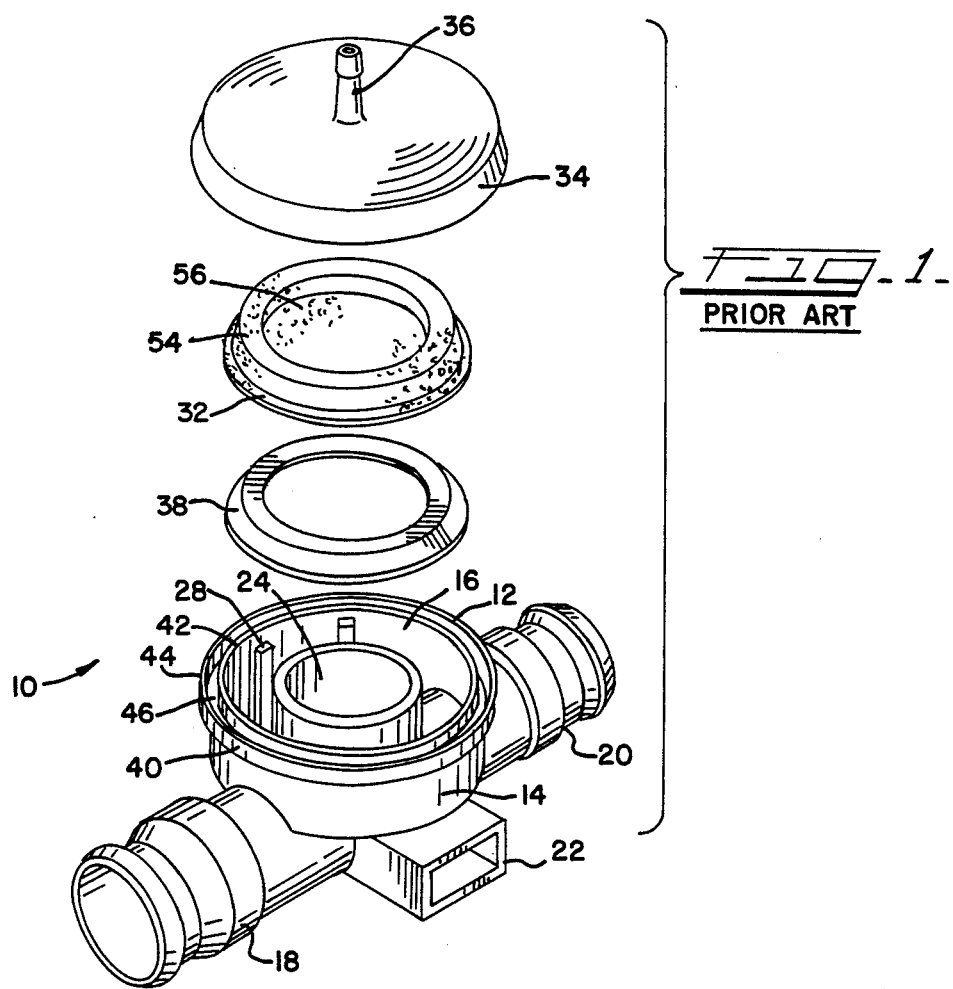
FIG. 1 is an exploded perspective view of the prior art exhalation valve assembly.
Figure 1A:
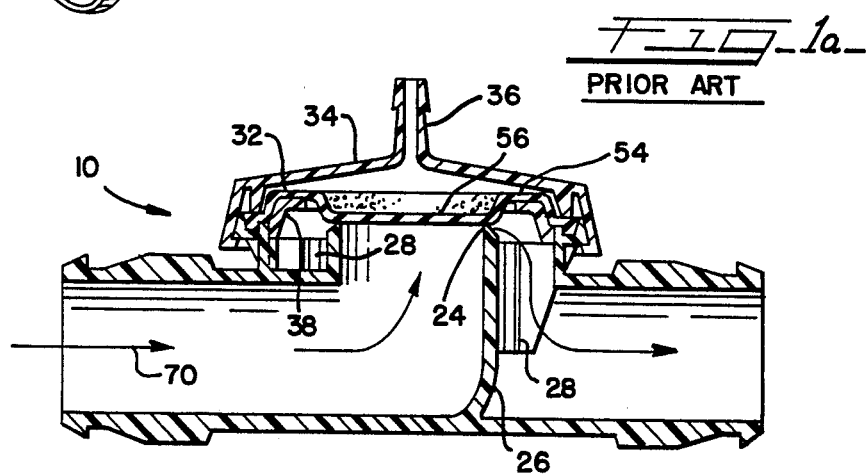
FIG. 1a is a cross section of the prior art exhalation valve assembly.

Referring to FIG. 1 and FIG. 1a, the valve assembly 10 of one prior art valve assembly is shown. This prior art valve assembly 10 is comprised of a valve body 12 forming a generally circular housing 14 defining a chamber 16. An inlet conduit 18 and an outlet conduit 20 are in flow communication with chamber 16. One end of the inlet conduit 18 includes a section 26 which extends into the chamber 16 and forms a circular gas discharge port 24. Disposed on the inside wall of the valve body 12 are a plurality of upwardly extending support members or struts 28. Such support members 28 are used to position a ring member 38 inside the housing 14. Also disposed on the valve body 12, adjacent the bottom thereof, is an outwardly extending and generally rectangular mounting support member 22. Such mounting support member 22 enables the valve assembly 10 to be attached to a support structure (not shown) and thereby held in a predetermined position.

The valve assembly 10 also includes a flexible, circular diaphragm member 32 that is disposed across the chamber 16. A cap or cover 34 snap locks onto the body 12 and holds the diaphragm 32 across the chamber 16. Centrally located on the cover 34 is a gas inlet port 36 that can be used to direct a gas into the assembly 10. The gas, however, does not flow into the chamber 16 but is directed into the area above diaphragm 32.

A circular plastic ring member 38 is disposed in the valve body 12 and rests on the support members 28. The ring member 38 is disposed adjacent the periphery of chamber 16 and circumferentially surrounds the gas discharge port 24. Once the ring member 38 is in position, the diaphragm 32 is placed over it. The diaphragm 32 includes an upwardly extending section 54 configured to arch over the ring member 38 and includes a generally circular section 56 that is used to selectively close-off the gas discharge port 24. The diaphragm 32 rests on a groove area 46 formed by an inner wall 42 and an outer wall 44 on the valve body 12. When the cover 34 is disposed over the diaphragm 32, it snap locks over lip 40.

The ring member 38 supports a portion of the diaphragm 32, thereby occluding such portion of the diaphragm 32 from extending across the chamber 16. In this way, the effective area of the diaphragm 32 over the chamber 16 is decreased, thereby decreasing the valve area ratio. Because of this, less pressure is required to raise the diaphragm 32 off of the gas discharge port 24.

Referring now to FIG. 2 and FIG. 2a, the valve assembly 100 of the present invention is shown. The valve assembly 100 is comprised of a valve body 112 forming a generally circular housing 114 defining a chamber 116. An inlet conduit 118 and an outlet conduit 120 are in flow communication with chamber 116. One end of the inlet conduit 118 includes a section 126 that extends into the chamber 116 and forms a circular gas discharge port 124. In the preferred embodiment, port 124 is circumferentially disposed in chamber 116. Located concentrically about and generally parallel to the walls of the discharge port 124 in the chamber 116 is a concentric tubular ring structure 128 integrally formed on valve body 112. Wall section 142 and wall section 144 are also integrally formed on the valve body 112 concentrically with the gas discharge port 124, but are not located within the chamber 116. Wall sections 142 and 144 define the exterior wall of the valve body 112. Thus, in effect, there are three concentric, generally parallel wall structures located about the discharge port 124; that is, moving out from discharge port 124 is the ring 128, the inner wall section 142, and the outer wall section 144. In the preferred embodiment, ring 128 extends above the top of wall sections 142 and 144.

The valve assembly 100 includes a circular, flexible diaphragm 132 that is disposed across the chamber 116. An outwardly extending annular seat 155 is disposed about the circumference of the diaphragm 132. The annular seat 155 rests in a grooved area 146 formed by the inner wall 142 and the outer wall 144. A cap or cover 134 snap locks onto the body 112 and holds the diaphragm 132 across the chamber 116. Centrally located on the cover 134 is a gas inlet port 136 that can be used to direct a gas into the assembly 100. As with the prior art assembly, the gas is not directed into the chamber 116 but is directed into the area above diaphragm 132.

The diaphragm 132 includes an upwardly extending section 154 that, in certain embodiments of the diaphragm, is designed to arch over the ring structure 128. A generally circular section 156 of the diaphragm is used to selectively close-off the gas discharge port 124. The concentric ring structure 128 takes the place of the support members 28 and ring member 38 previously described in FIG. 1 and discussed in the description of the prior art.

A wide variety of materials, shapes, and other configurations can be used in this invention. For example, in the preferred embodiment all of the parts of the present invention are made of a plastic material such as nylon, PVC, acrylic resins, and the like. Of course, other materials such as reinforced plastics or even metal are within the scope of the present invention. Further, the shape of the diaphragm and materials used to construct it can be modified so as to achieve various valve area ratios and pressure holding capabilities. This invention, therefore, is not to be limited to the specific embodiments discussed and illustrated herein.

Operation of the prior art valve assembly 10 and valve assembly 100 of the present invention will now be discussed. In one manner of operation, a patient connection hose (not shown) is secured to the gas inlet conduit 18. Likewise, an outlet hose (not shown) is secured to the gas outlet conduit 20. During inspiration, it is necessary to maintain a positive pressure above diaphragm 32. Therefore, a gas supply tube (not shown) is joined to the gas inlet port 36 on the cover 34 such that a gas is directed into the assembly 10 above the diaphragm 32, thereby enabling a positive pressure to be created above the diaphragm. During exhalation, it is sometimes desirable to maintain a positive pressure above the diaphragm 32, thus forcing the patient to exert an increased pressure in order to exhale through the valve assembly. The amount of increased pressure exerted is determined by the air pressure applied above the diaphragm and by the valve area ratio.

The operating principle of the valve assembly 100 of the present invention is similar to that of the prior art assembly. A patient connection hose is secured to the gas inlet conduit 118 and an outlet hose is secured to the gas outlet conduit 120. During inspiration, a positive pressure is maintained above diaphragm 132, and a gas supply tube (not shown) is joined to the gas inlet port 136 for this purpose. The gas is directed into the assembly 100 above the diaphragm 132, thereby enabling a positive pressure to be created above the diaphragm. Again, it is sometimes desirable to maintain a positive pressure above the diaphragm during exhalation, thus forcing the patient to exert an increased pressure in order to exhale through the valve assembly. Likewise, the air pressure applied above the diaphragm and the valve area ratio of the present invention determine the increased pressure exerted. It is to be understood, however, that in other applications of the prior art assembly and of the present invention, it may be desirable not to maintain such positive pressure. In such cases, no pressure would be maintained above the respective diaphragms during exhalation.

FIGS. 1a and 2a include arrows 70 which generally indicate the flow of gas exhaled from a patient as it would be directed through an embodiment of the respective valve assemblies. More specifically, when the patient exhales with sufficient pressure, the pressure above the respective diaphragms 32, 132 is overcome. This causes the diaphragms 32, 132 to disengage the ports 24, 124. The exhaled gas then flows through the inlet conduit 18, 118, through gas discharge ports 24, 124, and then into the chambers 16, 116. The exhaled gas would flow out of the chambers 16, 116 through the outlet conduit 20, 120. As indicated by FIG. 2a, the exhaled gas may flow on both sides of the ring structure 128. Depending on the diaphragm employed, the diaphragm may maintain contact with the ring structure 128 during exhalation, decreasing the effective area of the diaphgram. During inspiration, a positive pressure is created in the respective assemblies 10, 100 above diaphragms 32, 132 causing sections 56, 156 of the diaphragms 32, 132 to engage discharge ports 24, 124. This prevents gas from escaping from the patient circuit through the valve assembly. Air or other gas to the patient comes from the ventalator, which is connected to the patient circuit upstream from the valve assembly.

In the prior art valve assembly, the ring member 38 extended toward the center of the chamber 16 and in one embodiment supported a portion of the diaphragm 32. By acting as a support for a section of the diaphragm 32, the ring member 38 decreased the amount of force necessary to disengage the diaphragm 32 from the discharge port 24. If one desired to increase the force necessary to disengage the diaphragm 32 from the port 24, the ring member 38 could be removed and/or a different diaphragm or ring could be used. In the present invention, one may change the amount of force necessary to disengage the diaphragm 132 from the discharged port 124 by changing the configuration and/or the composition of the diaphragm 132. In this way, a diaphragm may be used that is partially supported by the ring member 128. Of course, one may also change the amount of force needed by changing the pressure of the gas directed above the diaphragm 132 via the gas inlet port 136. In this way, it is possible to achieve the benefits of the prior art valve assembly (achieving various valve area ratios utilizing the same valve assembly) without the need for a removable ring member.

What we claim is:

1. A valve assembly for use in a volume ventilator, said valve assembly comprising a valve body having an exterior wall in part defining a pressure chamber, a gas inlet conduit in flow communication with the pressure chamber, said gas inlet conduit forming a discharge port in said pressure chamber, a gas outlet conduit in flow communication with said pressure chamber for directing gas out of said pressure chamber, said outlet conduit being located concentrically around said discharge port, diaphragm means removably disposed in and extending across said valve body, said discharge port, said outlet conduit and said pressure chamber being on one side of said diaphragm means, said diaphragm means including a central portion engageable with said discharge port for selectively closing off said discharge port, said diaphragm means defining the remainder of said pressure chamber and further including an annular arched portion which is spaced radially from said central portion, and a cover having a gas inlet joined to the valve body and extending across the diaphragm means on the opposite side thereof from the pressure chamber, said cover engaging and clamping the outer periphery of said arched portion, said arched portion being spaced in the direction of said opposite side from said central portion and said outer periphery, a generally tubular ring structure joined to said valve body and located concentrically between said discharge port and said exterior wall and within the pressure chamber, said ring structure being separate from said exterior wall by a predetermined distance and extending into said pressure chamber such that the ring structure engages and supports said arched portion of the diaphragm means between the exterior wall and the discharge port and thereby decreases the effective area of the diaphragm means, said ring structure being spaced in the direction of said opposite side from said discharge port and said outer periphery and normally engaging said arched portion when said diaphragm means is in its relaxed position, flow passages being formed between said ring structure and said outer wall and between said ring structure and said discharge port.

2. A valve body according to claim 1 wherein said valve body is constructed of a plastic material and wherein the ring structure is an integral portion of the valve assembly.

3. A valve body according to claim 1 wherein said ring structure extends above said exterior wall.

4. A valve body according to claim 3 wherein said exterior wall is comprised of first and second sections, said cover forming one of said sections and said outer periphery of said diaphragm means is disposed between the other of said sections and said cover.

5. A valve assembly for use in a volume ventilator, said valve assembly comprising a valve body having an exterior wall in part defining a pressure chamber, a gas inlet conduit in flow communication with the pressure chamber, said gas inlet conduit foring a circular discharge port in said pressure chamber, a circular gas outlet conduit concentric with and around said discharge port and in flow communication with said pressure chamber for directing gas out of said pressure chamber, diaphragm means removably disposed in and extending across said valve body, said discharge port, said outlet conduit and said pressure chamber being on one side of said diaphragm means, said diaphragm means including a circular center portion for selectively engaging and closing off said discharge port, said diaphragm means having a circular shape and resting along its circumference on the exterior wall of the valve body and having an annular arcuate arched section concentrically disposed between said center portion and said circumference, said diaphragm means defining the remainder of said pressure chamber, and a cover having a gas inlet joined to the valve body and extending across the diaphragm means on the opposite side thereof from the pressure chamber, said cover clamping said circumference, and a generally tubular ring structure disposed within the pressure chamber, said ring structure being integrally formed on the valve body and disposed concentrically about and adjacent to the discharge port and separated from the exterior wall by a predetermined distance and thereby forming a flow passage between said ring structure and said exterior wall and forming a flow passage between said discharge port and said ring structure, said flow passage communicating with said discharge port, said ring structure being spaced in the direction of said opposite side from said discharge port and from said circumference of said diaphragm means, and said ring structure being engageable with and adapted to support said arched section of said diaphragm means when said diaphragm means is in its relaxed position.

6. The valve assembly of claim 5 wherein the tubular ring structure is located on the gas outlet conduit such that the ring structure supports said arched section of the diaphragm means and thereby decreases the effective area of the diaphragm means both when said center portion engages and is out of engagement.

* * * * *